United States Patent
Ross et al.

(10) Patent No.: US 11,062,807 B1
(45) Date of Patent: Jul. 13, 2021

(54) SYSTEMS AND METHODS FOR DETERMINING BIOMETRIC PARAMETERS USING NON-INVASIVE TECHNIQUES

(71) Applicant: MASSACHUSETTS MUTUAL LIFE INSURANCE COMPANY, Springfield, MA (US)

(72) Inventors: Gareth Ross, Amherst, MA (US); Sears Merritt, Groton, MA (US)

(73) Assignee: Massachusetts Mutual Life Insurance Company, Springfield, MA (US)

( * ) Notice: Subject to any disclaimer, the term of this patent is extended or adjusted under 35 U.S.C. 154(b) by 1103 days.

(21) Appl. No.: 15/382,268

(22) Filed: Dec. 16, 2016

Related U.S. Application Data

(60) Provisional application No. 62/387,170, filed on Dec. 23, 2015.

(51) Int. Cl.
*G16H 50/30* (2018.01)
*G06K 9/00* (2006.01)
(Continued)

(52) U.S. Cl.
CPC .......... *G16H 50/30* (2018.01); *A61B 5/0022* (2013.01); *A61B 5/1118* (2013.01); *A61B 5/14546* (2013.01); *A61B 5/150854* (2013.01); *A61B 5/4806* (2013.01); *A61B 5/6801* (2013.01); *A61B 5/7275* (2013.01); *G06K 9/00892* (2013.01)

(58) Field of Classification Search
CPC .... G16H 50/30; A61B 5/4806; A61B 5/6801; A61B 5/7275; A61B 5/0022; A61B 5/1118; A61B 5/150854; A61B 5/14546; G06K 9/00892
See application file for complete search history.

(56) References Cited

U.S. PATENT DOCUMENTS

| 5,337,750 A * | 8/1994 | Walloch | A61B 5/02225 600/493 |
| 2005/0209785 A1 * | 9/2005 | Wells | G16H 50/20 702/19 |

(Continued)

OTHER PUBLICATIONS

Yonei, Yohiskazu, et al. "The effects of walking with pedometers on quality of life and various symptoms and issues relating to aging." Anti-Aging Medicine 5.1 (2008): 22-29. (Year: 2008).*

(Continued)

*Primary Examiner* — Jonathan Durant
(74) *Attorney, Agent, or Firm* — Foley & Lardner LLP

(57) ABSTRACT

A method for assessing a user's health comprises receiving a first biometric parameter from the user's wearable device and determining whether the first biometric parameter was collected for a time period satisfying a time threshold. The method comprises, upon the time threshold being satisfied, calculating a second biometric parameter based on the first biometric parameter and/or user's health attributes provided by the user. The method comprises determining a health score for the user based on the health score, the first biometric parameter, and/or the second biometric parameter. The method further comprises transmitting and populating a user interface associated with the user with the health score, the first biometric parameter, and/or the second biometric parameter.

14 Claims, 6 Drawing Sheets

(51) Int. Cl.
*A61B 5/00* (2006.01)
*A61B 5/15* (2006.01)
*A61B 5/145* (2006.01)
*A61B 5/11* (2006.01)

(56) References Cited

U.S. PATENT DOCUMENTS

2008/0133572 A1* 6/2008 Verhey-Henke ....... G16H 10/20
2008/0171919 A1* 7/2008 Stivoric .................. A61B 5/01
 600/301
2011/0161100 A1* 6/2011 Peak ...................... G06Q 40/08
 705/2
2017/0286622 A1* 10/2017 Cox ........................ G06F 19/00

OTHER PUBLICATIONS

Ewald, Ben, Mark McEvoy, and John Attia. "Pedometer counts superior to physical activity scale for identifying health markers in older adults." British Journal of Sports Medicine 44.10 (2010): 756-761. (Year: 2010).*

* cited by examiner

SYSTEMS AND METHODS FOR DETERMINING BIOMETRIC PARAMETERS USING NON-INVASIVE TECHNIQUES

CROSS REFERENCE TO RELATED APPLICATIONS

This application claims priority to U.S. Provisional Patent Application Ser. No. 62/387,170, filed on Dec. 23, 2015, which is hereby incorporated by reference in its entirety.

TECHNICAL FIELD

The present disclosure relates in general to data transmission and analytics from hardware devices.

BACKGROUND

Many institutions require consumers to undergo medical examinations, which typically involve significant information gathering through a combination of acquiring data from consumers, questions answered during a paramedical exam, several physical measurements and collecting body fluids, and a medical examination by a physician. Traditionally, consumers have been presented an initial questionnaire or phone interviews, which typically ask questions related to lifestyle, health, personal medical history, family medical history, and the like. Usually as a next step in these traditional methods, a medical professional visits the consumer's home to acquire information by collecting vital statistics, urine sample, blood sample, and/or other invasive procedures to measure one or more bio-analytic parameter of the consumer. However, collecting this data is often a problem for the consumers for a variety of physical and/or psychological reasons, and is often a major barrier to institutions attempting to enroll new customers. More particularly, the consumers often do not want to have blood drawn at home for fear of needles, do not want to undergo medical screening, do not have the time, and many other reasons.

SUMMARY

For the aforementioned reasons, there needs to be a system and method for efficient and effortless collection and calculation of consumer biometric data. According to an embodiment, an analytical engine operates in a system that includes a user interface, external sources, an internal database, client computing devices, a communication network, and wearable devices. It should be understood that the system can include less components, more components, or different components depending on desired analysis goals.

In an embodiment, a method comprises receiving, by a server, a request for an assessment associated with a user. The method comprises receiving, by the server, a time threshold, wherein the time threshold corresponds to a minimum time associated with collection of health-related data. The method comprises receiving, by the server, from an electronic device a first biometric parameter, wherein the electronic device is in communication with a wearable device associated with the user, wherein the wearable device is configured to collect data associated with at least the first biometric parameter. The method comprises determining, by the server, whether a time period associated with the first biometric parameter satisfies the time threshold. The method comprises, upon the time period associated with the first biometric parameter satisfying the time threshold, calculating, by the sever, a second biometric parameter based at least on one of the first biometric parameter and one or more health attributes associated with the user, wherein the one or more health attributes associated with the user are provided by the user and received by the server. The method comprises determining, by the server, a health score associated with the user, wherein the health score is calculated based on at least one of the first and the second biometric parameters. The method further comprises transmitting, by the server, at least one of the health score and the second biometric parameter to the electronic device to populate one or more input field within a user interface associated with the electronic device.

In another embodiment a computers system comprises an electronic device in communication with a wearable device associated with a user and a server. The computer system comprises a wearable device configured to collect data associated with the at least a first biometric parameter. The computer system further comprises a server, which is configured to receive a request for an assessment associated with the user. The server is configured to receive a time threshold, wherein the time threshold corresponds to a minimum time associated with collection of health-related data. The server is configured to receive from the electronic device the first biometric parameter. The server is configured to determine whether a time period associated with the first biometric parameter satisfies the time threshold. The server is configured to, upon the time period associated with the first biometric parameter satisfying the time threshold, calculate a second biometric parameter based at least on one of the first biometric parameter and one or more health attributes associated with the user, wherein the one or more health attributes associated with the user are provided by the user and received by the server. The server is configured to determine a health score associated with the user, wherein the health score is calculated based on at least one of the first and the second biometric parameters. The server is further configured to transmit at least one of the health score and the second biometric parameter to the electronic device to populate one or more input field within a user interface associated with the electronic device.

Numerous other aspects, features and benefits of the present disclosure may be made apparent from the following detailed description taken together with the drawing figures.

BRIEF DESCRIPTION OF THE DRAWINGS

The present disclosure can be better understood by referring to the following figures. The components in the figures are not necessarily to scale, emphasis instead being placed upon illustrating the principles of the disclosure. In the figures, reference numerals designate corresponding parts throughout the different views.

DETAILED DESCRIPTION

Figure 1:
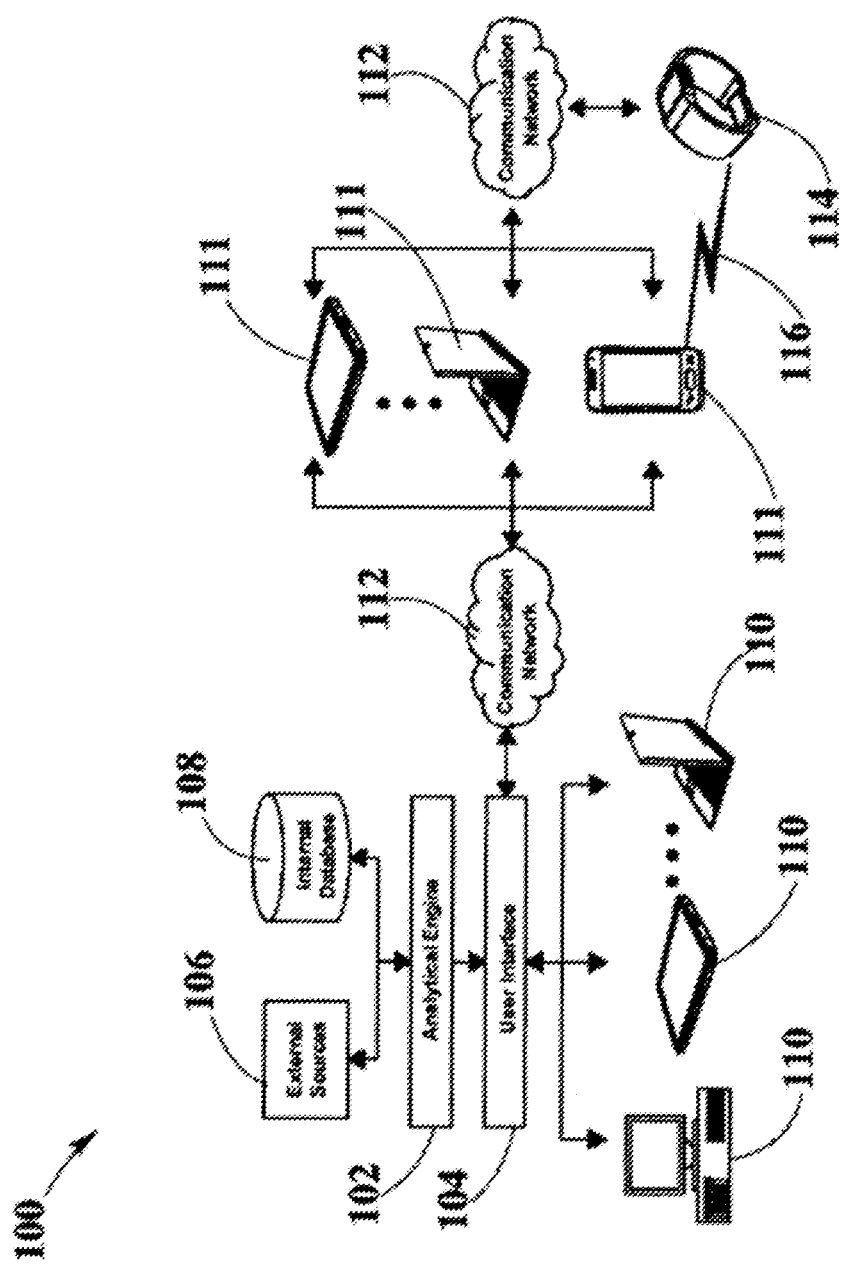
FIG. 1 is a block diagram illustrating a system for tracking, and processing at least one biometric parameter data, according to an embodiment.

Reference will now be made to the exemplary embodiments illustrated in the drawings, and specific language will be used here to describe the same. It will nevertheless be understood that no limitation of the scope of the invention is thereby intended. Alterations and further modifications of the inventive features illustrated here, and additional applications of the principles of the inventions as illustrated here, which would occur to one skilled in the relevant art and having possession of this disclosure, are to be considered within the scope of the invention.

As used here, the following terms may have the following definitions:

"Price" refers to a periodic payment that a consumer offers to a health-related institution.

"Scoring process" refers to the health assessment of a consumer. It quantifies the health that an institution may accept in exchange for the payment of a price.

"Wearable technology" may refer to a category of wearable devices worn by consumers including tracking information related to health and fitness.

"Agent" refers to an individual working for a company or as a broker with an interest in attracting new clients by analyzing their needs and wishes. An agent may specifically look for prospects with high referral potential. In addition, an agent may represent the intermediary between an issuing company and a consumer.

"Analytical engine" refers to a software module that handles data integration, breaks data streams into atomic parts, executes rules, and performs data matching by using fuzzy logic, among others.

The impact of wearables is already being felt in education, communication, navigating, and entertainment. However, the greatest potential of wearable devices may lie in healthcare. Wearables are able to track activity, fitness, and lifestyle. Therefore, wearable devices may have the potential to disrupt the health market in all sorts of ways.

System Components and Architecture

FIG. 1 is a block diagram illustrating a system for using a wearable device to collect at least one biometric parameter in lieu of using conventional paramedical sampling of blood or other invasively and non-invasively measured fluids. The disclosed system 100 may be owned by any health-related consumer protection company.

According to one embodiment, system 100 includes analytical engine server 102, user interface 104, external sources 106, internal database 108, client computing devices 110, communication network 112, wearables 114, and link 116. It should be understood that system 100 and analytical engine server 102 can include fewer components, more components, or different components depending on desired analysis goals.

According to an embodiment, analytical engine server 102 further includes one or more data extraction modules, one or more data processing modules, and one or more APIs. The modules and/or APIs contained/operating within analytical engine server 102 are further described in FIG. 3. The analytical engine server 102 may execute an analytical engine (not shown) that includes sub-components. Each of the sub-components within analytical engine may be a set of computer instructions executed by central processing units that run computer executable program instructions or related algorithms. The sub-components of the analytical engine may include a biometric parameter estimation engine (not shown) configured to estimate biometric parameters that are otherwise measured by parametric sampling from sensed biometric parameters, and predictive model engine (not shown) that may be configured to predict a mortality risk factor. The predictive model engine may be executed on a predictive model engine server, which, in one embodiment, is the same server as the analytical engine server 102. Alternatively, a server separate from the analytical engine server 102 may be used to execute the predictive model engine. Each central processing unit may be a component of computing devices such as a server, a single computer, or multiple computers in a distributed configuration. In an example, a central processing unit as described in FIG. 2 below can be implemented within the aforementioned computing devices.

In FIG. 1, analytical engine server 102 is operatively coupled to and in bi-directional communication with user interface 104, external sources 106, internal database 108, and client computing devices 110. User interface 104 is further operatively coupled to and in bi-directional communication with client computing devices 111 via communication network 112, and wearables 114 are wirelessly coupled to and in bi-directional communication with client computing devices 111 via link 116. Each of the different components of system 100 may be implemented in any type of suitable processor-controlled device that receives, processes, and/or transmits digital data, configured as further described below and in FIG. 2. Examples of devices incorporating one or more suitable processor-controlled devices include smartphones, desktop computers, laptop computers, servers, tablets, PDAs, specialized computing platforms biometric data processing, different algorithms, and the like. Examples of devices may include smartphones, desktop computers, laptop computers, tablets, and PDAs, among others. Examples of link 116 include any short-ranged wireless protocol, such as, for example Bluetooth, BTLE, Bluetooth Smart, Wi-Fi, Zigbee, and the like.

In FIG. 1, analytical engine server 102 may be implemented as software that runs on a server including a processing unit for running related algorithms or computer executable program instructions. Processing unit may include a processor with computer-readable medium, such as a random access memory (RAM) (not shown) coupled to the processor. Examples of processor may include a microprocessor, application specific integrated circuit (ASIC), and field programmable object array (FPOA), among others. In some embodiments, analytical engine server 102 receives data from external sources 106 and internal database 108. In these embodiments, analytical engine server 102 processes the received data and stores the processed data at internal database 108. In further embodiments, analytical engine server 102 generates user interface 104 in which a user, such as an underwriter and/or consumer, interacts with system 100 via client computing devices 110. Examples of data received from external sources 106 include data collected from an consumer wearing an activity sensor, such as a passive wearable device (e.g., Fitbit® device). The data collected from the external source 106 may include raw and/or processed data that includes estimated biometric data that would otherwise be collected by paramedical sampling and used to estimate a mortality risk factor. The biometric sensors may be of a wide variety to sense heart rate (e.g., heart rate monitor), sweat, oxygen levels, motion, steps (e.g., pedometer or smartphone with appropriate app), or otherwise.

In one or more embodiments, external sources 106 and internal database 108 are implemented as relational databases that provide functions of fetching, indexing, and storing data. External sources 106 and internal database 108 may be implemented through database management systems (DBMS), such as, MySQL, PostgreSQL, SQLite, Microsoft SQL Server, Microsoft Access, Oracle, SAP, dBASE, FoxPro, IBM DB2, LibreOffice Base, FileMaker Pro, and/or any other type of database that may organize collections of data.

In one or more embodiments, user interface 104 can be implemented as software that is configured to communicate with a user and that runs on any type of computing device. In these embodiments, user interface 104 may communicate with client computing devices 111 so as to allow users of system 100 to manage personal data. Examples of users of system 100 include agents, authorized personnel, employees associated with the health-related companies, and consumers that created an account within system 100.

In further embodiments, user interface 104 receives an application from analytical engine server 102 that is displayed on client computing devices 110. User interface 104 may grant access to other computing device operated by a user associated with the health-related consumer protection company in order to evaluate a health score for consumers based on biometric data received from the consumers. In still further embodiments, user interface 104 receives an application programming interface (API) from analytical engine server 102 that is displayed on client computing devices 111. User interface 104 may grant access to consumers to manage their user accounts within system 100. Examples of an application are further described in FIG. 4.

In one or more embodiments, wearables 114 are clothing and accessories incorporating computer and advanced electronic technologies. In these embodiments, wearables 114 read biometric data from one or more consumers, and send biometric data readings from one or more consumers to an application installed on client computing devices 111. Examples of biometric data of biometric parameters include activity, number of steps per day, heartbeat rates, levels of sweat, O2 saturation, and the like. Client computing devices 111 compute and send biometric data to the health-related consumer protection company via communication network 112. Examples of wearables 114 may include passive and/or active sensors, including smartwatches, Fitbit® or equivalent devices, trackers, pedometers, activity trackers, and the like. In one embodiment, a client computing device (e.g., smartphone) with the ability to sense and generate biometric data (e.g., number of steps) may be utilized, as well, thereby reducing or eliminating the need for a wearable device.

In an exemplary operation, analytical engine server 102 receives data from external sources 106. Analytical engine server 102 then processes sensed biometric data received from wearables 114 and creates estimated biometric data that is typically measured from collected paramedical samples and stored in internal database 108. Analytical engine server 102 manages accounts created by groups of consumers. Analytical engine server 102 may generate user interface 104 in which a user, such as, user associated with the analytical server and/or consumers may access with system 100 via client computing devices 110 and 111 via communication network 112. Analytical engine server 102 receives biometric data from members of groups of consumers using wearables 114. Analytical engine server 102 processes biometric data received from the consumers and produces statistics that can be used by groups of consumers reporting biometric data to the health-related consumer protection company. Analytical engine server 102 may also determine or estimate a health score or other related factors for the consumers along with information to populate in an application for a product or service based on the estimated biometric data and health score.

Figure 2:
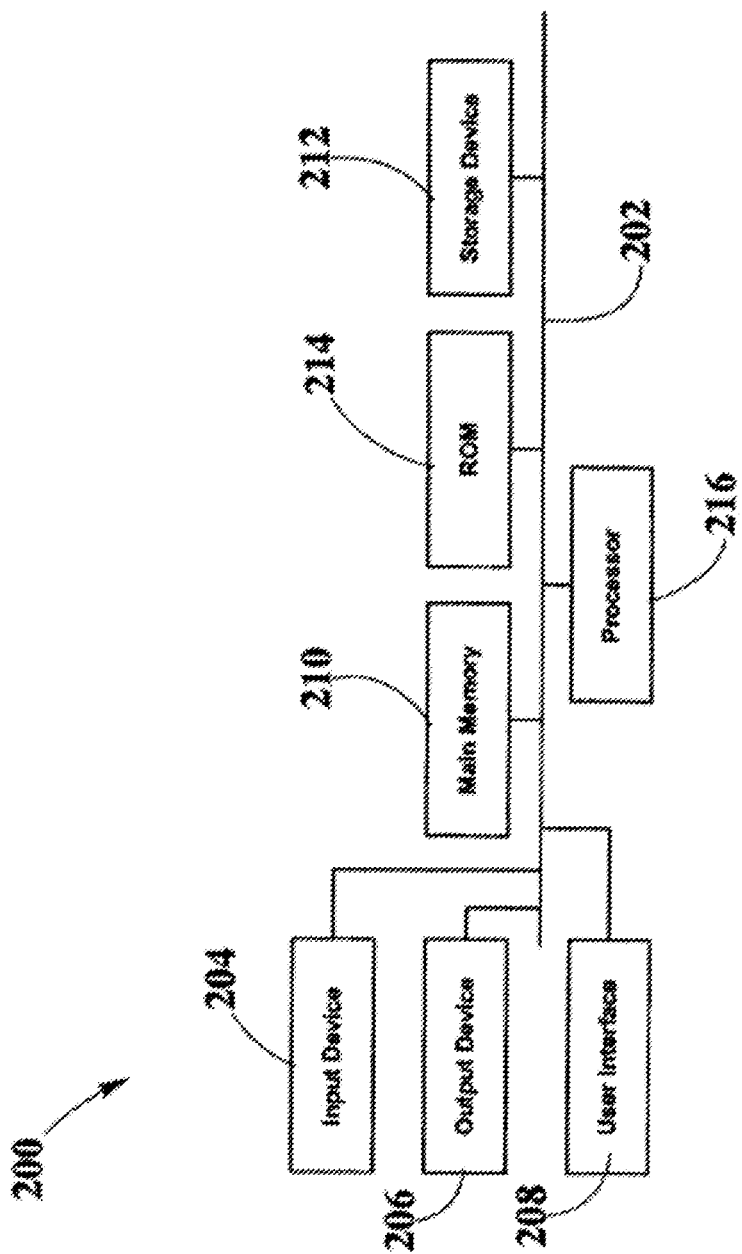
FIG. 2 is a block diagram of an exemplary computing device in which one or more embodiments of the present disclosure may operate, according to an embodiment.

FIG. 2 is a diagram of example components of computing device 200 or server, according to an exemplary embodiment. According to some aspects of this embodiment, computing device 200 includes bus 202, input device 204, output device 206, user interface 208, main memory 210, storage device 212, read only memory (ROM 214) and processor 216. In another exemplary embodiment, server includes additional, fewer, different, or differently arranged components than are illustrated in FIG. 2.

In one embodiment, bus 202 coordinates the interaction and communication among the components of the server. Input device 204 includes a mechanism that permits a user to input information to computing device 200, such as a keyboard, a mouse, a button, a pen, a touch screen, voice recognition and/or biometric mechanisms, etc. Output device 206 includes a mechanism that outputs information to the operator, including a display, a light emitting diode (LED), and a speaker, among others.

User interface 208 enables computer interactions with other devices and/or systems via a network connection. Network connections may refer to any suitable connection between computers such as intranets, local area networks (LAN), cloud networks, virtual private networks (VPN), wireless area networks (WAN), and the Internet, among others.

Main memory 210 includes a random access memory (RAM) or another type of dynamic storage device that may store information and instructions for execution by processor 216. ROM 214 includes a ROM device or another type of static storage device that may store static information and instructions for use by processor 216. Processor 216 includes a microprocessor, an application specific integrated circuit (ASIC), and a field programmable object array (FPOA), among others, that may interpret and execute instructions.

According to some aspects of this embodiment, server, using one or more suitable software modules, enables data fetching, biometrics processing tasks, statistical processing, estimating analytics, and predictive analytics. The server performs these operations in response to processor 216 executing software instructions contained in a computer-readable medium, such as main memory 210.

The software instructions reads into main memory 210 from another computer-readable medium, such as storage device 212, or from another device via user interface 208. The software instructions contained in main memory 210 may cause processor 216 to perform processes that will be described later. Alternatively, hardwired circuitry may be used in place of or in combination with software instructions to implement processes described herein. Thus, implementations described herein are not limited to any specific combination of hardware circuitry and software.

Figure 3:
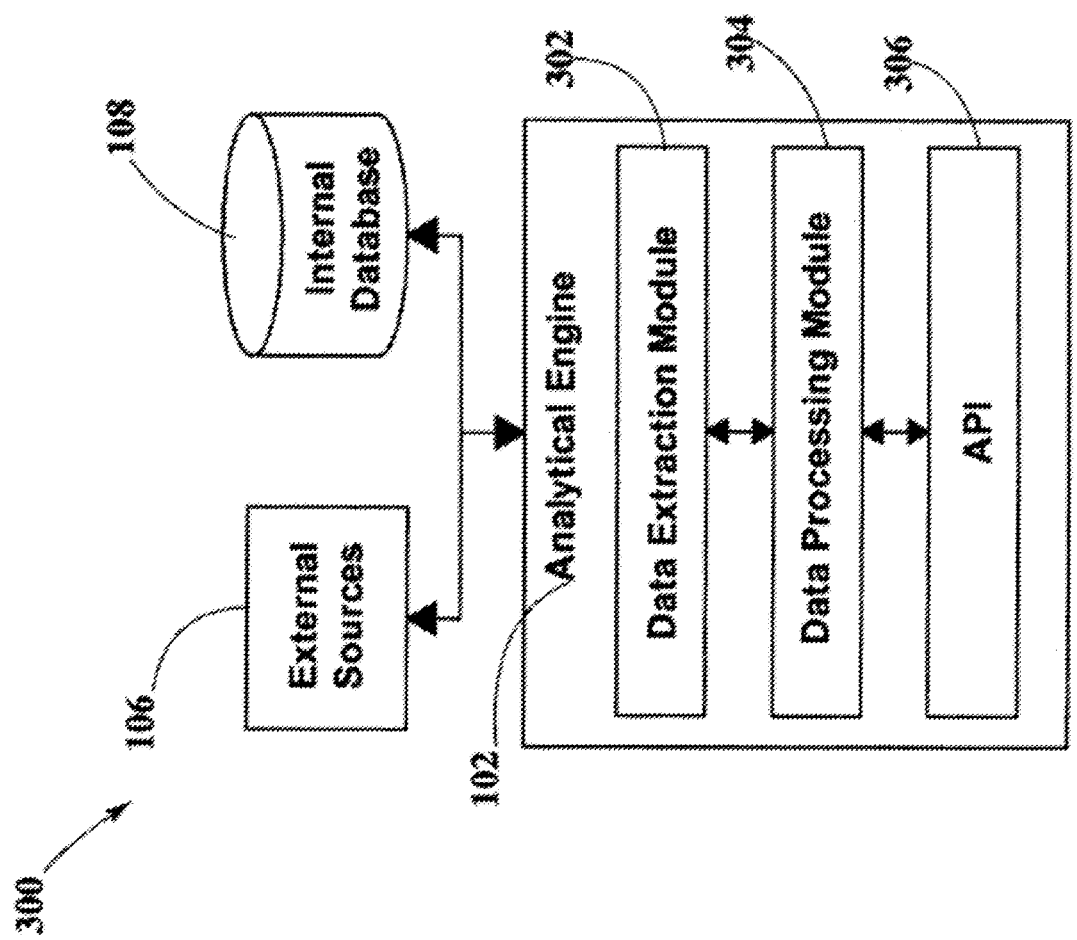
FIG. 3 is a block diagram illustrating a portion of the system pertaining to an analytical engine, according to an embodiment.

FIG. 3 is a block diagram illustrating a subsystem of the system pertaining to analytical engine server 102 of FIG. 1. In FIG. 3, subsystem 300 includes external sources 106, internal database 108, analytical engine server 102, data extraction module 302, data processing module 304, and API 306. It should be understood that subsystem 300 can include less components, more components, or different components depending on the desired analysis goals. In an example, external sources 106, internal database 108, analytical engine server 102, data extraction module 302, data processing module 304, and API 306 are implemented as external sources, internal database, analytical engine, data extraction module, data processing module, and API described in system 100 of FIG. 1.

Analytical engine server 102 may execute an analytical engine (not shown) and be operatively coupled to and in bi-directional communication with data extraction module 302, data processing module 304, and API 306. Analytical engine server 102 is further operatively coupled to and in bi-directional communication with external sources 106 and internal database 108.

In one or more embodiments, data extraction module 302 resides within analytical engine server 102, and is implemented as one or more computer software modules that include programmatic rules or executing/running different algorithms that allow data fetching and data indexing of collected data from wearable devices over one or more time periods.

In one or more embodiments, data processing module 304 resides within analytical engine server 102, and is implemented as one or more computer software modules that include programmatic rules or executing/running different algorithms that allow data fetching, data indexing, and data storing of biometric and estimated biometric data, along with historical or standards data collected from clinical studies or by other consumers at a previous time, may be performed by data extraction module 302. In these embodiments, data processing module 304 may be configured to estimate or predict biometric parameter(s) that would ordinarily be measured through samples collected in a paramedical process. The estimation or prediction may be performed using statistical processes, including correlation, k-nearest neighbor, and other statistical processes that enable biometric parameters to be estimated as a function of biometric parameter(s) measured by a wearable device.

In one or more embodiments, API 306 within analytical engine server 102 is any Representational State Transfer Application Programming Interface (REST API) that controls and manages one or more APIs. In these embodiments, API 306 provides web services to one or more mobile applications installed on the client computing devices. Examples of web services include showing data on a website, uploading large amounts of data that will later be consumed by a mobile app, downloading data to run custom analytics, exporting data, and the like.

Figure 4:
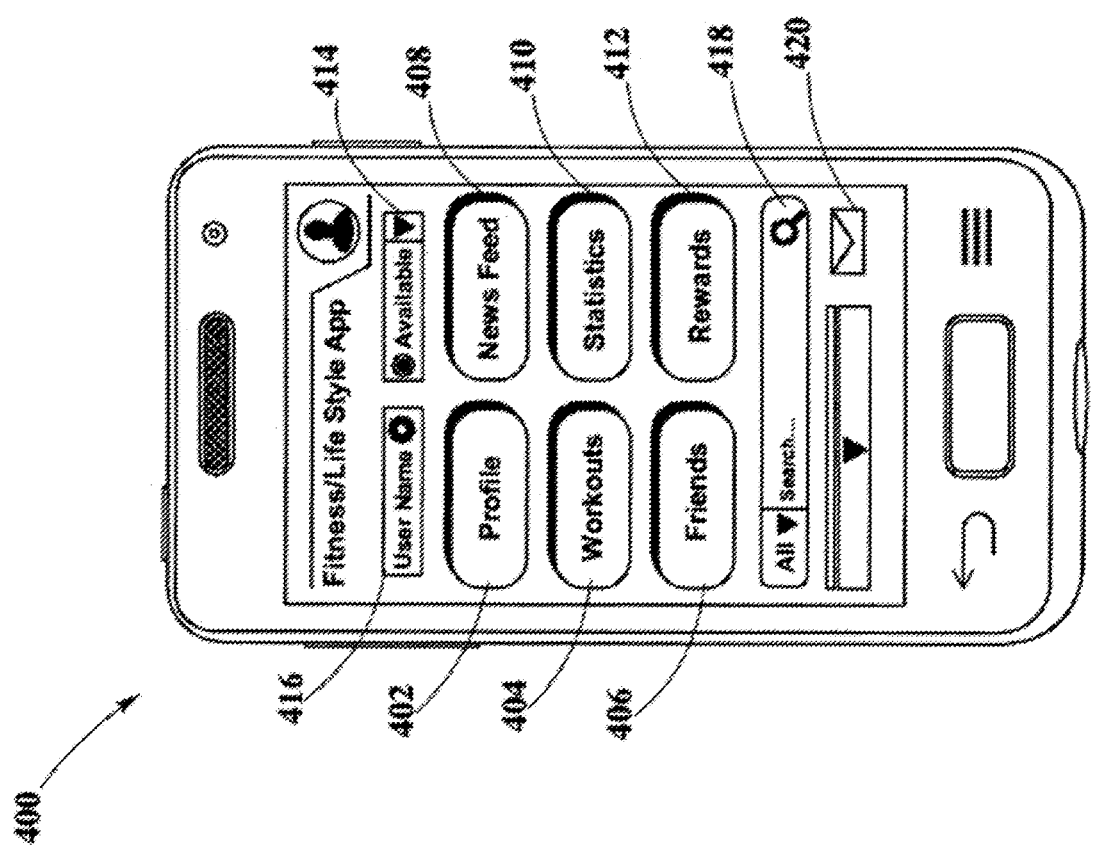
FIG. 4 is an exemplary illustration of a user interface of a mobile application for managing the fitness/lifestyle of consumers, including tracking activity, according to an embodiment.

FIG. 4 is an exemplary illustration of a user interface of a mobile application for monitoring fitness/lifestyle of consumers. In FIG. 4, mobile application 400 includes profile 402, workouts 404, friends 406, news feed 408, statistics 410, rewards 412, status 414, user name 416, search 418, and email 420. It should be understood that mobile application 400 can include fewer fields, more fields, or different fields depending on the desired analysis goals.

In FIG. 4, mobile application 400 is implemented as software that can be downloaded and installed on client computing devices, such as smartphones or wearables of consumers, and be configured to interact with the system of an health-related consumer protection company. Examples of mobile application 400 are GUI applications (Fitness/LifeStyle App) that may be available at, downloaded, and installed from a public software app stores or digital application distribution platforms, such as Apple iTunes®, Google Play® Store and Amazon.com®, among others. In these embodiments, mobile application 400 includes the following illustrative functions: allowing the user to create and manage a user account in the health-related consumer protection company's system profile 402; allowing the user to see the available workouts 404; allowing the user to invite and look at friends list 406; allowing the user to look at friends activity news feed 408; allowing the user to look at workout history of the user and/or friends statistics 410; allowing the user to check rewards for achieving goals 412; allowing the user to perform searches of people to send friend requests to 418; allowing the user to see the user name of the person connected to the system 416; allowing the user to receive emails from the health-related consumer protection company system 420; and allowing the user to see connection status 414. In one embodiment, the mobile application 400 may enable the user to view activity levels (e.g., via workouts 404), which may include all activities, including sleeping) collected by wearable devices or an electronic device on which the mobile application is operating over days, weeks, or months.

In some embodiments, a plurality of processes that are part of the assessing consumer's health are performed by one or more computing devices, such as computing device 200, which may be controlled by the analytical engine server 102. The methods are implemented with components of the exemplary operating environments of FIGS. 1-4. The steps of this exemplary method are embodied in a computer readable medium containing computer readable code such that the steps are implemented when the computer readable code is executed by a computing device. While the blocks in the disclosed processes are shown in a particular order, the actual order may differ. In some embodiments, some steps may be performed in parallel.

Figure 5:
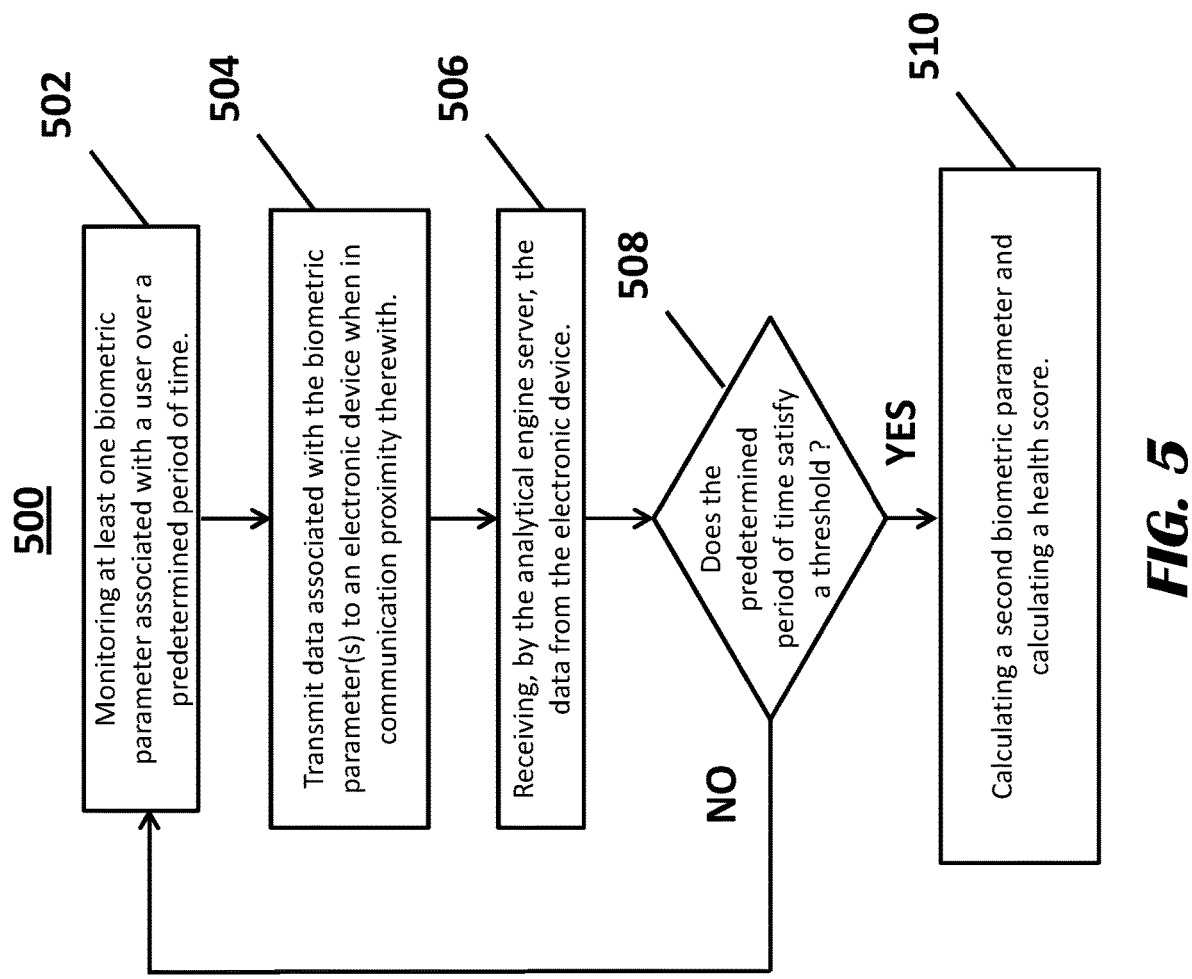
FIG. 5 is a flowchart of an illustrative process of evaluating a consumer using non-invasive biometric parameter sensing techniques.

With regard to FIG. 5, a flowchart of an illustrative process 500 of assessing a consumer using non-invasive techniques is shown. Invasive techniques may include drawing blood samples, but for the purposes of this description, may include collecting urine samples, stool samples, or other samples of bodily fluids or tissue that are used for determining a consumer health score. In other words, the non-invasive techniques may be used as a substitute for collecting paramedical data, and may include measuring one set of biometric parameters and estimating another set of biometric parameters that would typically be measured from a paramedical process.

The process 500 may start at step 502, where a wearable electronic device may sense/monitor at least one biometric parameter of a user over a predetermined period of time. The biometric parameter(s) may include activity, sleep, and/or other biometric parameter. The predetermined period of time may be three months or other time period that may be used to provide an accurate measure of a user for use in predicting other biometric parameter(s) that would otherwise be measured using paramedical processes. In some embodiments, the period of time is pre-determined and received by the analytical engine server from a user operating a client computing device associated with the analytical engine server. The time period may signify the minimum amount of time needed to collect data from the wearable. A person skilled in the relevant art will appreciate that the time period may be different for each respective biometric category or type. For example, the sleep pattern time period may be one month (e.g., the data collected must be for at least one month) and the time period for physical activity may be set at three months (data must be collected for at least a three-month time period). At step 504, data associated with the sensed/monitored biometric parameter(s) may be transmitted to a networked device when the wearable electronic device is in communication proximity therewith. The transmission may utilize any number of communications protocols, including wireless and wired communications protocols, as understood in the art. The networked device may be a mobile electronic device associated with a user associated with the health-related consumer protection company and configured to communicate with the wearable device and the analytical engine server. In some embodiments, at step 506, the networked device may transmit the data to an analytical engine server, where the data may be stored in a database or other data repository in a data record associated with the user during the duration of the predetermined period of time. The analytical server may receive a request from the networked device for a health assessment of a consumer. Upon receiving this request, the analytical engine server may also receive the data gathered by the wearable device.

At step 508, the analytical engine server may determine whether the pre-determined time threshold (explained above) is satisfied. If the analytical engine server determined that the time threshold is not satisfied, the process continues to step 502. Otherwise, as explained below, at step 510 the analytical engine server may predict at least a second biometric parameter, and a health score of the consumer by applying the calculated second biometric parameter(s) using a predictive model.

Figure 6:
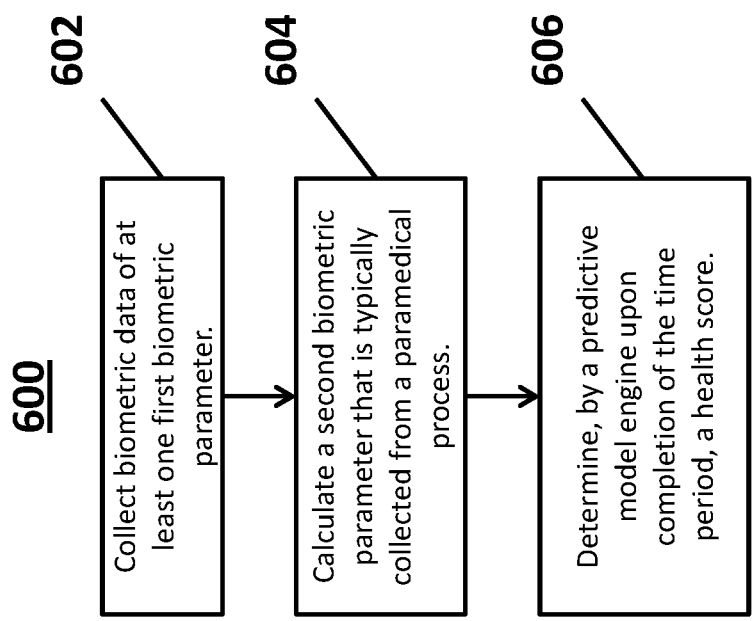
FIG. 6 is a flowchart of an illustrative process of evaluating a consumer using non-invasive biometric.

With regard to FIG. 6, a flowchart of a process 600 of assessing a consumer using non-invasive techniques is shown. The process 600 may start at step 602 by the analytical engine server 102 collecting biometric data of the at least one first biometric parameter over at least one time period from a wearable device, where the wearable device may be configured to collect data associated with at least one biometric parameter from a consumer. The biometric parameter(s) may include activity data. A health-related consumer protection company may provide the wearable device or the consumer may have his or her own wearable device. The biometric parameter(s) may include activity data, inactivity data (e.g., sleep), number of steps, heart rate, blood sugar level, energy usage, movement, or any other dynamic biometric measurement or combination thereof, as understood in the art. The time period(s) may be a certain number of months, such as three, that include sub-time periods, such as one month, week(s), and day(s) defined by smaller time periods, such as work commuting times, sleep times, mornings, afternoons, work periods, workout times, and so forth. Biometric parameter(s) may be collected over a longer time period to provide a more complete understanding of a user's health.

At step 604, the analytical engine server may calculate at least one second biometric parameter that is typically measured from samples (e.g., blood, urine, stool, etc.) collected by paramedical procedures. The calculations may include a variety of mathematical estimation processes, such as correlation, regression, pattern recognition (e.g., k-nearest neighbor algorithm), or any other mathematical algorithm, as understood in the art. The estimation may optionally utilize answers to a questionnaire, such as family medical history, to improve the estimate(s) of the biometric parameters typically determined from paramedical sampling. The questionnaire may be conventional or may include additional information, such as typical activities that may be correlated to sensed biometric parameter(s). Such activities may include profession, workout types, hobbies, and so forth. A person skilled in the relevant art will appreciate that in calculating the second biometric parameter, the analytical engine may also utilize the first biometric data received, and compare it to an existing database, which is configured to collect health-related data. For example, the analytical engine server may receive a biometric data from a user associated with the user's sleep time and number of steps taken in a typical day; the analytical engine server may then, determine a second biometric parameter (e.g., cholesterol level) based on the data gathered for other users within the same age, height, weight, family history of cholesterol levels, heart problems, and the like, with similar sleep patterns and physical activity level.

At step 606, the analytical engine server may determine a health score for the consumer based on the first and the second biometric parameter(s) as a function of the first biometric parameter(s) over the time period(s). The health score may be based on estimated biometric data of the biometric parameter(s).

In one embodiment, an application document may be automatically populated with the estimated biometric parameters and/or consumer health score. For example, a health-related application (e.g., a user interface on the networked device of an agent, or a web application associated with the user) may be populated with estimated cholesterol level(s), blood sugar level, health scores, and so forth, that are estimated based on biometric parameter measured using a wearable device. The analytical engine server may also determine one or more health-related products for the consumer based on the health score or the estimated biometric metrics, as understood in the art. The auto population of the application may include data that is or is not presented to the consumer. In one embodiment, the estimated data may be stored in association with the consumer, but only be available to a computing device associated with the analytical engine server 102.

The sensing by the wearable device may be made of activities (e.g., sleep, work, exercise) of the consumer during time period(s). One aspect may include providing a mobile app to be downloaded to a mobile device of the consumer, where the mobile device may be selectively in wireless communication with the wearable device. The mobile application may be configured to collect the biometric data being captured by the wearable device, and communicate the biometric parameter to a database for processing by an analytical engine server, for example, as provided in FIGS. 1-4. The communications may be performed continuously, periodically (e.g., daily), or aperiodically (e.g., when the wearable and/or mobile device are/is being charged).

As a result of estimating biometric parameter(s) of consumers that is typically collected by a paramedical process, the invasive collecting of paramedical data may be reduced or eliminated. Historical assessments using the process 500 may ultimately provide for refined other health assessments and scoring.

The foregoing method descriptions and the process flow diagrams are provided merely as illustrative examples and are not intended to require or imply that the steps of the various embodiments must be performed in the order presented. As will be appreciated by one of skill in the art the steps in the foregoing embodiments may be performed in any order. Words such as "then," "next," etc. are not intended to limit the order of the steps; these words are simply used to guide the reader through the description of the methods. Although process flow diagrams may describe the operations as a sequential process, many of the operations may be performed in parallel or concurrently. In addition, the order of the operations may be re-arranged. A process may correspond to a method, a function, a procedure, a subroutine, a subprogram, etc. When a process corresponds to a function, its termination may correspond to a return of the function to the calling function or the main function.

The various illustrative logical blocks, modules, circuits, and algorithm steps described in connection with the embodiments disclosed here may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

The actual software code or specialized control hardware used to implement these systems and methods is not limiting of the invention. Thus, the operation and behavior of the systems and methods were described without reference to the specific software code being understood that software and control hardware can be designed to implement the systems and methods based on the description here.

When implemented in software, the functions may be stored as one or more instructions or code on a non-transitory computer-readable or processor-readable storage medium. The steps of a method or algorithm disclosed here may be embodied in a processor-executable software module which may reside on a computer-readable or processor-readable storage medium. A non-transitory computer-readable or processor-readable media includes both computer storage media and tangible storage media that facilitate transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage or other magnetic storage devices, or any other tangible storage medium that may be used to store desired program code in the form of instructions or data structures and that may be accessed by a computer or processor. Disk and disc, as used here, include compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

When implemented in hardware, the functionality may be implemented within circuitry of a wireless signal processing circuit that may be suitable for use in a wireless receiver or mobile device. Such a wireless signal processing circuit may include circuits for accomplishing the signal measuring and calculating steps described in the various embodiments.

The hardware used to implement the various illustrative logics, logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

Any reference to claim elements in the singular, for example, using the articles "a," "an" or "the," is not to be construed as limiting the element to the singular.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the following claims and the principles and novel features disclosed herein.

What is claimed is:

1. A method comprising:
    receiving, by a server, a request for an assessment associated with a user;
    receiving, by the server, a time threshold, wherein the time threshold corresponds to a minimum time associated with collection of data associated with the user;
    receiving, by the server, from an application executing on from an electronic device of the user a first biometric parameter measuring an aspect of the user's physical activity level, wherein the electronic device establishes an electronic communication with a wearable device associated with the user and receives the first biometric parameter from the wearable device, wherein the wearable device is configured to collect data associated with at least the first biometric parameter;
    determining, by the server, whether a time period associated with the first biometric parameter satisfies the time threshold;
    training, by the server, a machine learning computer model using data pertaining to other users having similar characteristics as the user;
    upon the time period associated with the first biometric parameter satisfying the time threshold, executing, by the sever, the machine learning computer model to calculate a second biometric parameter based at least on one of the first biometric parameter and one or more health attributes associated with the user, wherein the one or more health attributes associated with the user are provided by the user, wherein the second biometric parameter is the user's cholesterol level or is derived from the user's cholesterol level; and determining, by the server, a health score associated with the user, wherein the health score is calculated based on at least one of the first and the second biometric parameters.

2. The method of claim 1, further comprising:

transmitting, by the server, at least one of the health score and the second biometric parameter to a web application associated with the user to populate one or more input field within the web application.

3. The method of claim 1, wherein the first biometric parameter is associated with the user's sleep.

4. The method of claim 1, wherein the second biometric parameter is calculated by applying a k-nearest neighbor predictive method.

5. The method of claim 1, wherein the wearable device associated with the user is a passive sensor.

6. The method of claim 1, wherein the communication between the electronic device and the wearable device associated with the user occurs periodically.

7. The method of claim 1, further comprising:

determining, by the server, one or more health-related products based at least one of the health score, first biometric parameter, and the second biometric parameter.

8. A computer system comprising:

an electronic device in communication with a wearable device associated with a user and a server;

a wearable device configured to collect data associated with the at least a first biometric parameter; and a server configured to:

receive a request for an assessment associated with the user;

receive a time threshold, wherein the time threshold corresponds to a minimum time associated with collection of health-related data;

receive from an application executing on the electronic device the first biometric parameter, wherein the first biometric parameter measures an aspect of the user's physical activity level, and wherein the electronic device establishes an electronic communication with the wearable device and receives the first biometric parameter from the wearable device;

determine whether a time period associated with the first biometric parameter satisfies the time threshold;

train a machine learning computer model using data pertaining to other users having similar characteristics as the user;

upon the time period associated with the first biometric parameter satisfying the time threshold, execute the machine learning computer model to calculate a second biometric parameter based at least on one of the first biometric parameter and one or more health attributes associated with the user, wherein the one or more health attributes associated with the user are provided by the user and received by the server, wherein the second biometric parameter is the user's cholesterol level or is derived from the user's cholesterol level; and determine a health score associated with the user, wherein the health score is calculated based on at least one of the first and the second biometric parameters.

9. The computer system of claim 8, wherein the server is further configured to:

transmit at least one of the health score and the second biometric parameter to a web application associated with the user to populate one or more input field within the web application.

10. The computer system of claim 8, wherein the first biometric parameter is associated with the user's sleep.

11. The computer system of claim 8, wherein the second biometric parameter is calculated by applying a k-nearest neighbor predictive method.

12. The computer system of claim 8, wherein the wearable device associated with the user is a passive sensor.

13. The computer system of claim 8, wherein the communication between the electronic device and the wearable device associated with the user occurs periodically.

14. The computer system of claim 8, wherein the one or more health attributes correspond to the user's family health history.

* * * * *